US008901512B2

(12) United States Patent
Fujita et al.

(10) Patent No.: US 8,901,512 B2
(45) Date of Patent: Dec. 2, 2014

(54) PARTICLE DETECTOR

(75) Inventors: Hideaki Fujita, Osaka (JP); Haruki Kamiyama, Osaka (JP); Kazushi Fujioka, Osaka (JP); Hiroki Okuno, Osaka (JP)

(73) Assignee: Sharp Kabushiki Kaisha, Osaka (JP)

( * ) Notice: Subject to any disclaimer, the term of this patent is extended or adjusted under 35 U.S.C. 154(b) by 0 days.

(21) Appl. No.: 14/239,900

(22) PCT Filed: Jun. 15, 2012

(86) PCT No.: PCT/JP2012/065352

§ 371 (c)(1),
(2), (4) Date: Feb. 20, 2014

(87) PCT Pub. No.: WO2013/035408

PCT Pub. Date: Mar. 14, 2013

(65) Prior Publication Data

US 2014/0166903 A1    Jun. 19, 2014

(30) Foreign Application Priority Data

Sep. 9, 2011 (JP) ................................. 2011-197196

(51) Int. Cl.
  *G01J 1/58*  (2006.01)
  *G21H 3/02*  (2006.01)
  *G01N 21/64*  (2006.01)

(52) U.S. Cl.
  CPC .......... *G01N 21/6486* (2013.01); *G01N 21/645* (2013.01); *G01N 2021/6463* (2013.01); *G01N 2021/6421* (2013.01)
  USPC ..................................... 250/458.1; 250/462.1

(58) Field of Classification Search
  USPC .......................................... 250/458.1, 462.1
  See application file for complete search history.

(56) References Cited

U.S. PATENT DOCUMENTS

| 7,030,970 B2 * | 4/2006 | Lin et al. .......................... 356/28 |
| 7,030,981 B2 * | 4/2006 | Bishop et al. .................. 356/368 |
| 7,671,987 B2 * | 3/2010 | Padmanabhan et al. ...... 356/338 |
| 2001/0009541 A1 * | 7/2001 | Ueyanagi .................. 369/112.23 |
| 2003/0170732 A1 | 9/2003 | Yogi et al. |
| 2012/0008143 A1 * | 1/2012 | Ihlefeld et al. ................ 356/335 |

FOREIGN PATENT DOCUMENTS

| JP | 61-129555 A | 6/1986 |
| JP | 2000-111477 A | 4/2000 |
| JP | 2002-55051 A | 2/2002 |
| JP | 2003-149154 A | 5/2003 |
| JP | 2008-145276 A | 6/2008 |

OTHER PUBLICATIONS

Official Communication issued in International Patent Application No. PCT/JP2012/065352, mailed on Jul. 10, 2012.

* cited by examiner

*Primary Examiner* — David Porta
*Assistant Examiner* — Mindy Vu
(74) *Attorney, Agent, or Firm* — Keating & Bennett, LLP

(57) ABSTRACT

There is provided a particle detector that can increase a detection sensitivity to fluorescence emitted from biogenic particles. A particle detector for detecting biogenic particles includes a substrate having a principal surface and configured to collect the biogenic particles on the principal surface, a light emitting element configured to irradiate particles collected on the principal surface with excitation light, and a light receiving element configured to receive fluorescence emitted from the particles when the particles are irradiated with the excitation light from the light emitting element. An optical axis of the Fresnel lens and a ray direction of the excitation light intersect with each other. The principal surface is a mirror surface.

1 Claim, 13 Drawing Sheets

FIG. 2
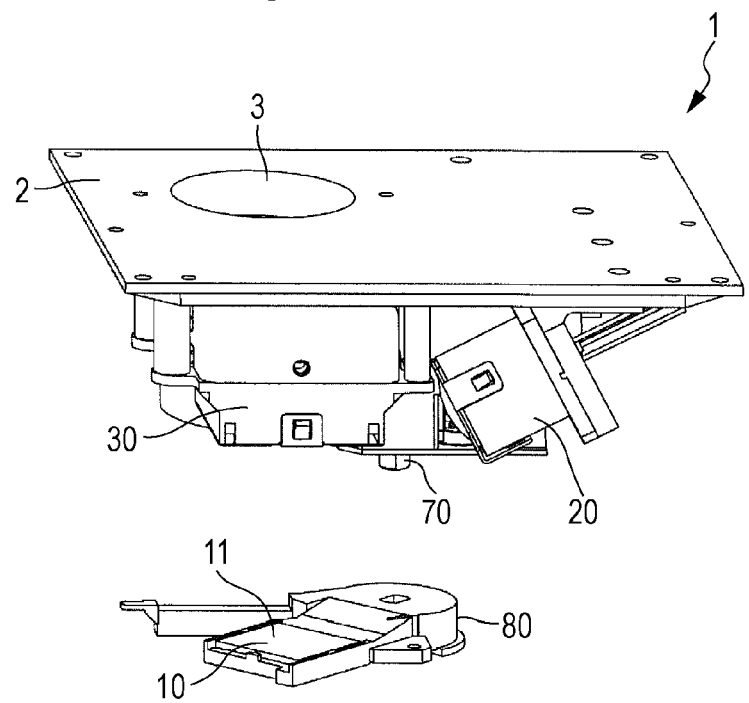
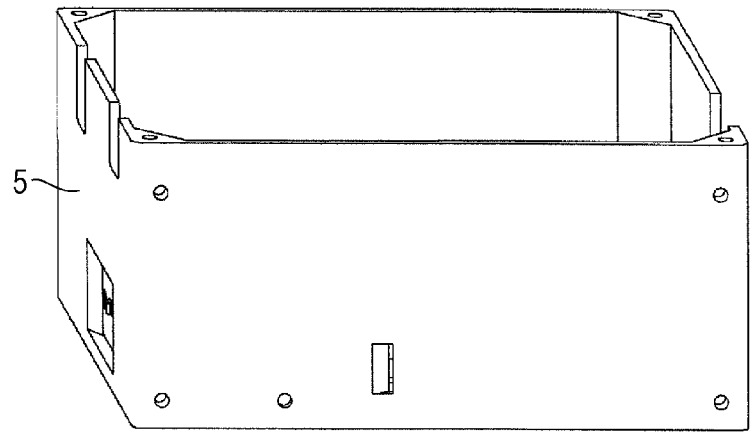
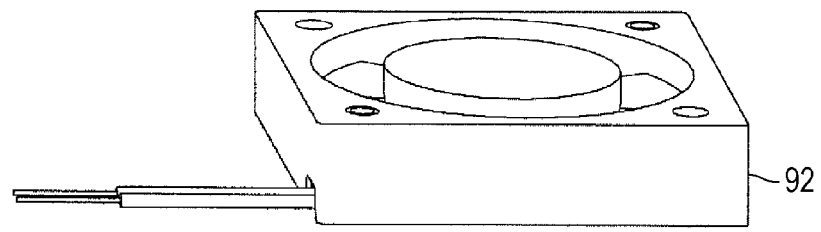

PARTICLE DETECTOR

TECHNICAL FIELD

The present invention relates to a particle detector, and more particularly, to a particle detector that detects biogenic particles.

BACKGROUND ART

There has hitherto been proposed an apparatus that measures the number of microorganisms existing in a specimen by staining the specimen with a fluorescent staining reagent and irradiating the specimen with excitation light to emit fluorescence (see, for example, Japanese Unexamined Patent Application Publication No. 2008-145276 (PTL 1)). In the apparatus disclosed in Japanese Unexamined Patent Application Publication No. 2008-145276 (PTL 1), the excitation light applied to the specimen and the fluorescence emitted from the specimen are coaxial with each other, the fluorescence is caused to arrive via a filter at an optical system for receiving the fluorescence, and the excitation light is removed by the filter.

CITATION LIST

Patent Literature

PTL 1: Japanese Unexamined Patent Application Publication No. 2008-145276

SUMMARY OF INVENTION

Technical Problem

In the method for detecting fluorescence from biogenic particles by irradiating the particles with excitation light, when the excitation light reaches a light receiving unit, it becomes noise and decreases the detection sensitivity to fluorescence in the light receiving unit. There is a limit to separation of the excitation light by only the filter, and sufficient detection sensitivity to fluorescence is sometimes not obtained. Also, since the filter needs to be additionally provided, the size and cost of the apparatus increase.

The present invention has been made in view of the above problems, and a main object of the invention is to provide a particle detector that can improve a detection sensitivity to fluorescence emitted from biogenic particles.

Solution to Problem

A particle detector according to the present invention detects biogenic particles, and includes a collecting member having a principal surface and configured to collect the biogenic particles on the principal surface, a light irradiation unit configured to irradiate the particles collected on the principal surface with excitation light, and a light receiving unit configured to receive fluorescence emitted from the particles when the particles are irradiated with the excitation light from the light irradiation unit. An optical axis of the light receiving unit and a ray direction of the excitation light intersect with each other. The principal surface is a mirror surface.

In the particle detector, preferably, the fluorescence is specularly reflected by the principal surface.

In the particle detector, preferably, the light irradiation unit includes an edge-emitting semiconductor laser element, and the semiconductor laser element has a multilayer structure including a light emitting layer, and is disposed such that a stacking direction of the multilayer structure is parallel to the principal surface.

In the particle detector, preferably, the light receiving unit includes a light collecting lens, and the light collecting lens contains a material that absorbs the excitation light.

In the particle detector, preferably, the light collecting lens is a Fresnel lens.

In the particle detector, preferably, the following relationship is established:

$$T = (B/\cos\theta + L)/2 \tan\theta$$

where $\theta$ represents an incident angle of the excitation light on the principal surface, $L$ represents a diameter of the light collecting lens, $T$ represents a distance between the light collecting lens and the principal surface, and $B$ represents a diameter of the excitation light.

Advantageous Effects of Invention

According to the particle detector of the present invention, it is possible to increase the detection sensitivity to fluorescence emitted from biogenic particles.

BRIEF DESCRIPTION OF DRAWINGS

FIG. 2 is a perspective view illustrating an exploded state of the particle detector illustrated in FIG. 1.

DESCRIPTION OF EMBODIMENTS

Figure 1:
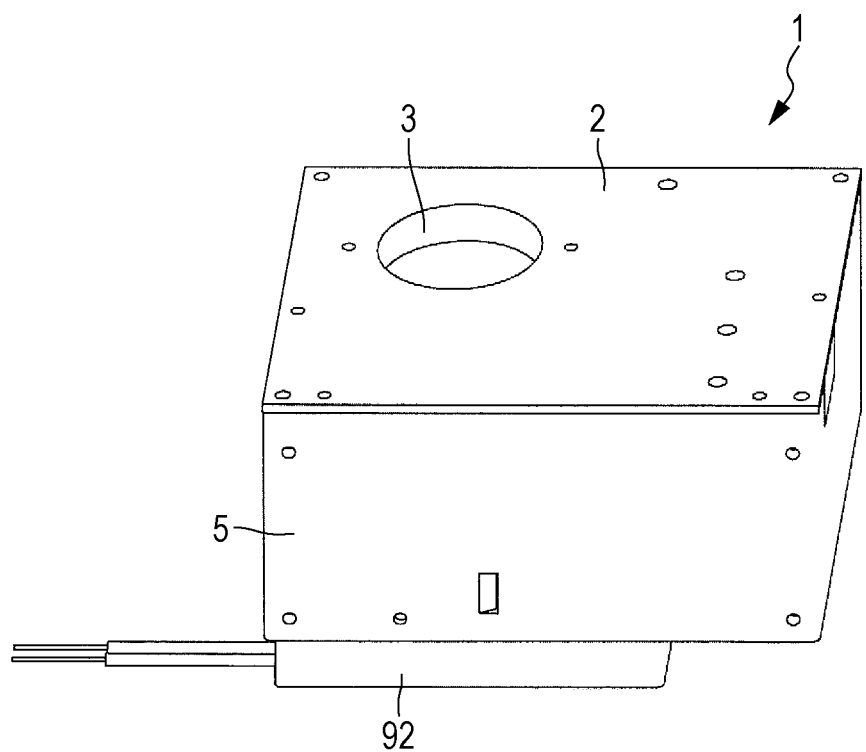
FIG. 1 is a perspective view illustrating an appearance of a particle detector according to an embodiment.

An embodiment of the present invention will be described below with reference to the drawings. In the following drawings, the same or corresponding parts are denoted by the same reference numerals, and descriptions thereof are not repeated.

[Overall Configuration of Particle Detector]

Figure 3:
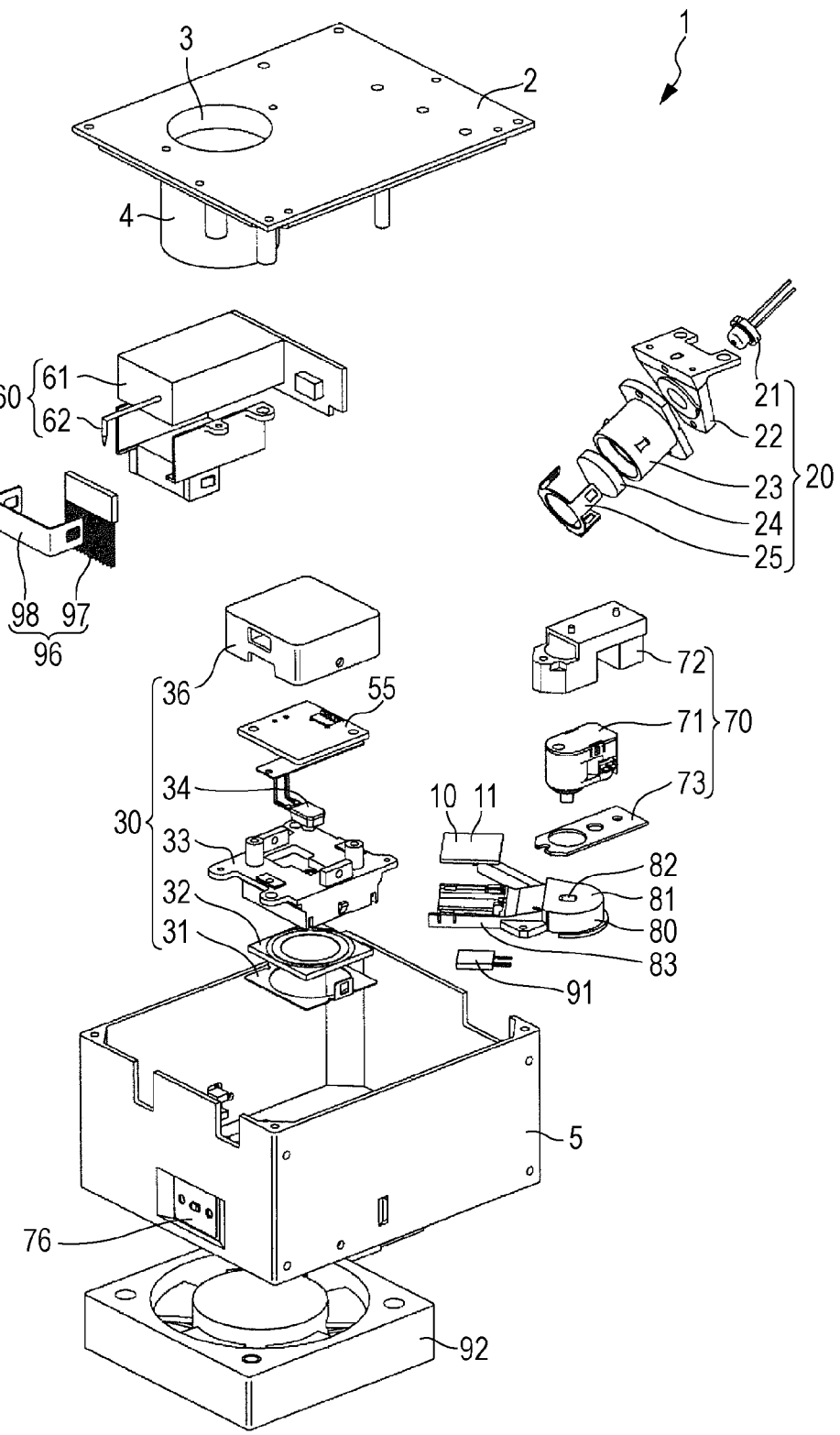
FIG. 3 is an exploded perspective view illustrating a detailed configuration of the particle detector.

FIG. 1 is a perspective view illustrating an appearance of a particle detector 1 according to the embodiment. FIG. 2 is a perspective view illustrating an exploded state of the particle detector 1 of FIG. 1. FIG. 3 is an exploded perspective view illustrating a detailed configuration of the particle detector 1. The particle detector 1 of the embodiment is an apparatus that detects biogenic particles such as pollen, microorganisms, and mold.

The particle detector 1 of the embodiment includes an upper cabinet 2 serving as a first housing, and a lower cabinet 5 serving as a second housing. The upper cabinet 2 is shaped like a substantially rectangular flat plate. The lower cabinet 5 is shaped like a substantially rectangular parallelepiped container having a bottom and opening in one direction. The upper cabinet 2 and the lower cabinet 5 are assembled such that the upper cabinet 2 closes the opening of the lower cabinet 5 like a lid, so that a hollow cabinet having an outer shape like a substantially rectangular parallelepiped is formed.

Devices that constitute the particle detector 1, such as a collecting unit 60, an excitation optical system 20, a light receiving optical system 30, and a cleaning unit 96, except for a fan 92, are contained in the cabinet. As an example, the cabinet has a size of 60 mm×50 mm (length and width of the upper cabinet 2)×30 mm (height).

A collecting cylinder 4 serving as a cylindrical member is provided integrally with the upper cabinet 2. The collecting cylinder 4 is shaped like a hollow cylinder, and extends from the upper cabinet 2 into the inside of the particle detector 1 while being attached at one end to a lower surface of the upper cabinet 2. The upper cabinet 2 has an introducing portion 3 that penetrates a part of the upper cabinet 2 in a thickness direction. The outside of the particle detector 1 and the inside of the collecting cylinder 4 communicate with each other via the introducing portion 3. The collecting cylinder 4 is provided to surround a below-described electrostatic probe 62. Air containing particles is introduced from the introducing portion 3 into the collecting cylinder 4. The collecting cylinder 4 guides the air containing particles toward a substrate 10 positioned opposed to the electrostatic probe 62.

A fan 92 is attached to an outer side of a bottom surface of the lower cabinet 5. The bottom surface of the lower cabinet 5 to which the fan 92 is attached has an aperture. This aperture opens to include an area opposed to the collecting cylinder 4 and an area opposed to a below-described brush 97, and is continuously formed by the area opposed to the collecting cylinder 4 and the area opposed to the brush 97.

The fan 92 can be rotationally driven in a forward direction and a reverse direction. When the fan 92 is driven in the forward direction, air in an inner space of the particle detector 1 is exhausted out of the particle detector 1 through the fan 92. When the fan 92 is driven in the reverse direction, air outside the particle detector 1 is introduced into the inner space of the particle detector 1 through the fan 92. The fan 92 is used for collection of particles into the particle detector 1, cooling of the particles after heating, and cleaning of the substrate 10 for collecting the particles. This reduces the size and cost of the particle detector 1.

The particle detector 1 includes a collecting unit 60. The collecting unit 60 collects particles contained in air onto a principal surface 11 of a substrate 10 serving as a collecting member. The collecting unit 60 includes a collection power-supply circuit 61 formed by a high-voltage power supply, and an electrostatic probe 62 serving as a discharge electrode. The substrate 10 has the principal surface 11. The substrate 10 is provided as a collecting member that collects, onto the principal surface 11, particles in which biogenic particles and powder dust, such as lint of chemical fiber, are mixed.

The substrate 10 is formed by a silicon flat plate. On the principal surface 11 of the substrate 10 for adsorbing particles, a conductive transparent coating is provided. The substrate 10 is not limited to silicon, but may be formed of glass, a ceramic material, or metal. The coating is not limited to the transparent coating, but, for example, a metallic coating may be provided on the surface of the substrate 10 formed of a ceramic material. When the substrate 10 is formed of metal, it is unnecessary to form a coating on the surface of the substrate 10. As long as the substrate 10 is a silicon substrate, the material itself is inexpensive, and it is easy to conduct mirror finishing on the principal surface 11 and to form the conductive coating on the principal surface 11.

The collection power-supply circuit 61 is provided as a power supply part that produces a potential difference between the substrate 10 and the electrostatic probe 62. The electrostatic probe 62 extends from the collection power-supply circuit 61, penetrates the collecting cylinder 4, and reaches an inner portion of the collecting cylinder 4. The substrate 10 is disposed opposed to the electrostatic probe 62. In this embodiment, the electrostatic probe 62 is electrically connected to a positive electrode of the collection power-supply circuit 61. The coating provided on the principal surface 11 of the substrate 10 is electrically connected to a negative electrode of the collection power-supply circuit 61.

The electrostatic probe 62 may be electrically connected to the positive electrode of the collection power-supply circuit 61, and the coating provided on the substrate 10 may be connected to a ground potential. Alternatively, the electrostatic probe 62 may be electrically connected to the negative electrode of the collection power-supply circuit 61, and the coating provided on the substrate 10 may be electrically connected to the positive electrode of the collection power-supply circuit 61.

When the fan 92 is driven in the forward direction, air in the cabinet of the particle detector 1 is exhausted, and simultaneously, air outside the cabinet is introduced toward the substrate 10 through the collecting cylinder 4. At this time, when a potential difference is produced between the electrostatic probe 62 and the substrate 10 by the collection power-supply circuit 61, particles in the air are positively charged around the electrostatic probe 62. The positively charged particles are moved to the substrate 10 by electrostatic force, are adsorbed by the conductive coating provided on the principal surface 11 of the substrate 10, and are thereby collected on the substrate 10.

In this way, in the particle detector 1 of the embodiment, particles are collected on the substrate 10 by charge collection utilizing electrostatic force. In this case, it is possible to reliably hold the particles on the substrate 10 during detection of the particles and to easily remove the particles from the substrate 10 after detection of the particles. By using the needle-like electrostatic probe 62 as a discharge electrode, the charged particles can be adsorbed on the surface of the substrate 10 opposed to the electrostatic probe 62 and in an extremely narrow region corresponding to an irradiation region of a below-described light emitting element. This allows adsorbed microorganisms to be efficiently detected in a fluorescence measuring step.

The particle detector 1 includes an excitation optical system 20 and a light receiving optical system 30. The excitation optical system 20 functions as a light irradiation unit that irradiates particles collected on the principal surface 11 of the substrate 10 with excitation light. The light receiving optical system 30 functions as a light receiving unit that receives fluorescence emitted from the particles with irradiation with excitation light from the excitation optical system 20. The excitation optical system 20 and the light receiving optical system 30 constitute a fluorescence detection unit that detects fluorescence emitted from the particles collected on the substrate 10. The excitation optical system 20 and the light receiving optical system 30 carry out measurement of fluorescence emitted from the particles collected on the substrate 10 before and after the particles are heated.

The excitation optical system 20 includes a light emitting element 21 serving as a light source, an exciting portion frame 22 and 23, a light collecting lens 24, and a lens presser 25. As the light emitting element 21, a semiconductor laser element for emitting blue laser light with a wavelength of 405 nm is used. Alternatively, an LED (Light Emitting Diode) may be used as the light emitting element 21. The wavelength of light emitted from the light emitting element 21 may be in an ultraviolet range or a visible range as long as the light excites biogenic particles to cause fluorescence emission from the particles.

The light receiving optical system 30 includes a metallic noise shield 36, a light receiving element 34, a light-receiving portion frame 33, a Fresnel lens 32, and a lens presser 31. As the light receiving element 34, a photodiode or an image sensor is used, for example. Between the light receiving element 34 and the noise shield 36, an amplifying circuit 55 is disposed to amplify signals detected by the light receiving element 34.

A cleaning unit 96 removes particles from the principal surface 11 of the substrate 10. The cleaning unit 96 includes a brush 97 serving as a cleaner, and a brush fixing portion 98. The cleaning unit 96 is fixedly supported on the collection power-supply circuit 61.

The brush 97 is formed by a fiber assembly having conductivity. For example, the brush 97 is formed of carbon fiber. The fiber diameter of the fiber assembly that forms the brush 97 is preferably within a range of 0.05 to 0.2 mm. One end of the brush 97 is supported by the brush fixing portion 98, and the other end thereof is a free end hanging from the brush fixing portion 98. As the brush 97 moves relative to the substrate 10 with the free end of the brush 97 being in contact with the principal surface 11 of the substrate 10, particles are removed from the substrate 10.

The collector for removing particles from the substrate 10 is not limited to the brush 97. For example, the collector may be a wiper shaped like a flat plate in contact with the principal surface 11 of the substrate 10, or a nozzle for jetting air toward the principal surface 11 of the substrate 10.

The particle detector 1 further includes a holding member 80 on which the substrate 10 is mounted and held, and a driving unit 70 serving as a moving mechanism for moving the substrate 10. The driving unit 70 includes a rotary motor 71 to be rotationally driven, a motor holder 72 for holding the rotary motor 71, and a motor presser 73 for positioning the rotary motor 71.

The holding member 80 includes a rotary base 81. The rotary base 81 is formed of a resin material having low thermal conductivity. The rotary base 81 has a shaft hole 82. By inserting an output shaft of the rotary motor 71 in the shaft hole 82, the rotary motor 71 and the rotary base 81 are coupled to each other. Upon driving of the rotary motor 71, the rotary base 81 rotates (forward, in reverse) about the position of the shaft hole 82.

The holding member 80 includes an arm 83 extending away from a rotation shaft of the rotary base 81. The arm 83 extends in a radial direction orthogonal to the rotation shaft of the rotary base 81, and has a frame-shaped portion at a distal end thereof. The frame-shaped portion has a shape such as to be able to receive the substrate 10. The substrate 10 is mounted on the holding member 80 by being received in the frame-shaped portion provided at the distal end of the arm 83.

The particle detector 1 includes a heater 91 serving as a heating unit. The heater 91 is disposed on a back surface of the substrate 10, and heats particles collected on the principal surface 11 of the substrate 10. The heater 91 is stuck on the back surface of the substrate 10. The heater 91 moves together with the substrate 10 during rotation of the rotary base 81. To the heater 91, a plurality of lines, including a power supply line to the heater 91 and a signal line of a sensor incorporated in the heater 91, are connected. These lines are led out of the cabinet of the particle detector 1.

A position sensor 76 is disposed on a side surface of the lower cabinet 5. The substrate 10 is moved in the cabinet of the particle detector 1 by rotation of the rotary motor 71. The position sensor 76 is provided to detect the current position of the substrate 10.

[Structure of Fluorescence Detecting Unit]

Figure 4:
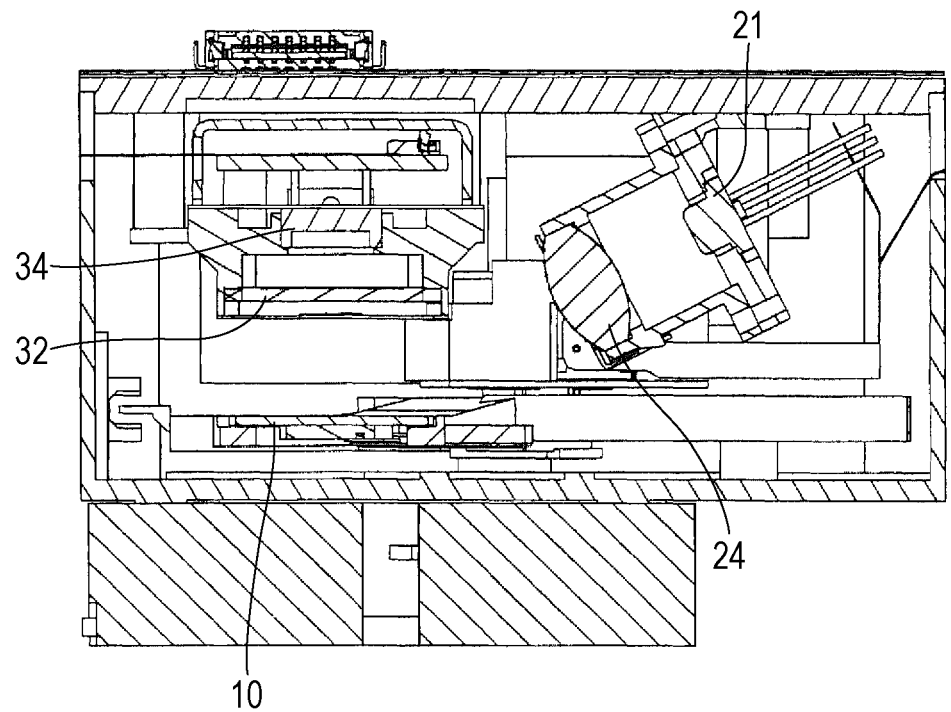
FIG. 4 is a cross-sectional view of the particle detector.
Figure 5:
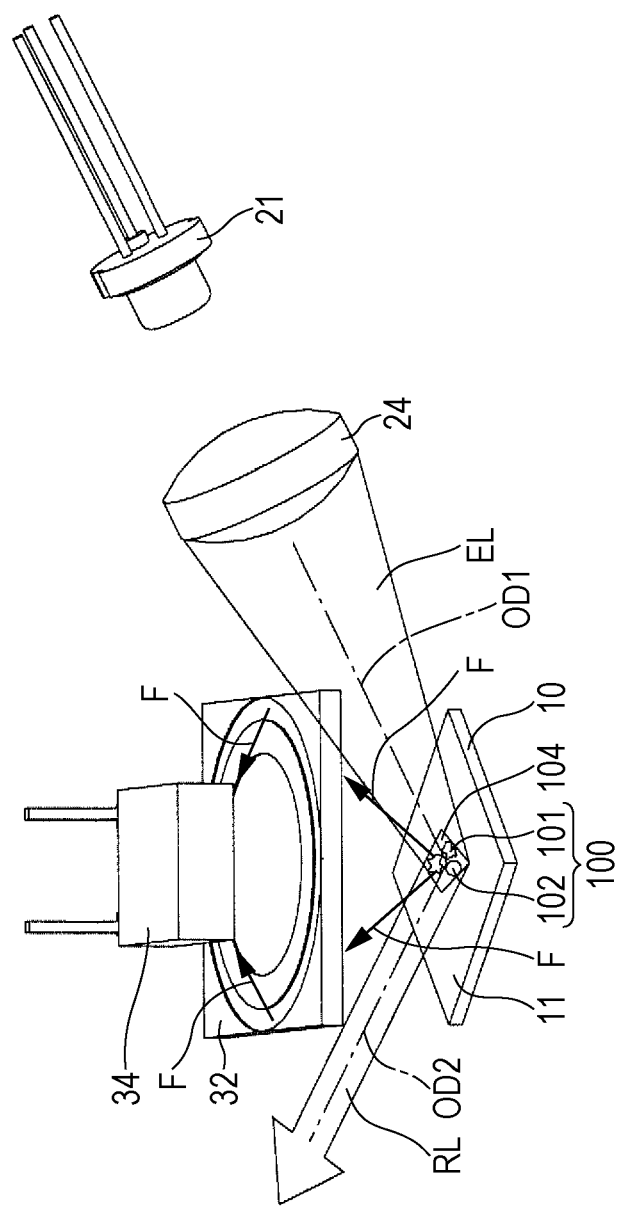
FIG. 5 schematically illustrates the behavior of light in an optical system included in the particle detector.
Figure 6:
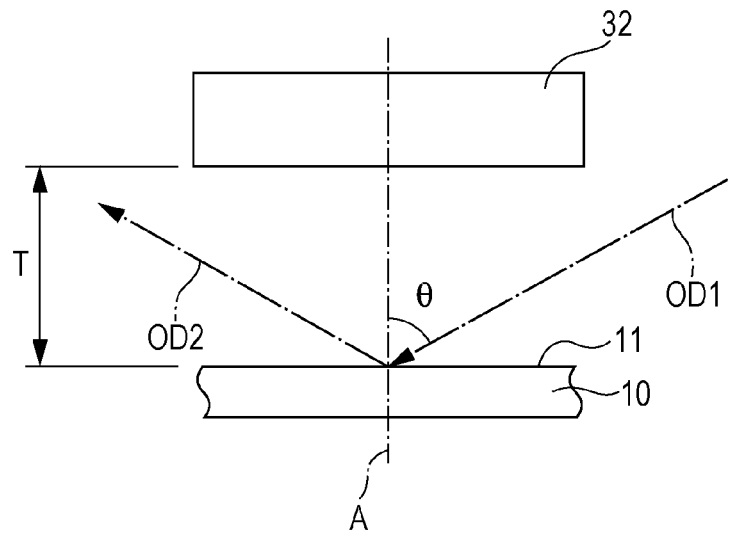
FIG. 6 schematically illustrates light reflection on a principal surface of a substrate.

FIG. 4 is a cross-sectional view of the particle detector 1. FIG. 5 schematically illustrates the behavior of light in the optical system included in the particle detector 1. FIG. 6 schematically illustrates light reflection on the principal surface 11 of the substrate 10.

As described above, the excitation optical system 20 for irradiating the principal surface 11 of the substrate 10 with excitation light includes the light emitting element 21 and the light collecting lens 24. Excitation light EL produced by the light emitting element 21 formed by a semiconductor laser element is collected through the light collecting lens 24, and is applied onto an excitation-light irradiation region 104 on the principal surface 11 of the substrate 10. The excitation light EL obliquely enters the principal surface 11 of the substrate 10. In FIGS. 5 and 6, a one-dot chain line denoted by symbol OD1 represents a ray direction of the excitation light EL. Here, the ray direction refers to a direction in which a luminous flux component of light (in this case, excitation light EL) travels. In other words, the ray direction OD1 of the excitation light EL is an optical axis of the excitation optical system 20.

The principal surface 11 of the substrate 10 is a mirror surface. The excitation light EL incident on the principal surface 11 at an incident angle θ is specularly reflected by the principal surface 11. Light obtained by regular reflection of the excitation light EL on the principal surface 11 forms reflected light RL. In FIGS. 5 and 6, a one-dot chain line denoted by symbol OD2 represents a ray direction of the reflected light RL. Since the excitation light EL is obliquely incident on the principal surface 11 of the substrate 10, the reflected light RL specularly reflected by the principal surface 11 is also obliquely reflected by the principal surface 11.

In FIG. 6, a one-dot chain line denoted by symbol A represents an optical axis of the light receiving optical system 30, that is, an optical axis of the Fresnel lens 32. The ray direction OD1 of the excitation light EL and the ray direction OD2 of the reflected light RL intersect the optical axis A. The ray directions OD1 and OD2 are at an angle to the optical axis A. The ray directions OD1 and OD2 are at an angle to an extending direction of the principal surface 11 of the substrate 10. FIG. 6 also shows a distance T between the principal surface 11 of the substrate 10 and the Fresnel lens 32.

Since the principal surface 11 is formed as a mirror surface, stray light is prevented from being caused by scattering of the excitation light EL on the principal surface 11. For this reason, it is possible to prevent the detection accuracy of the particle detector 1 from being reduced by the stray light as noise. When the principal surface 11 is a mirror surface, little scattering light is produced at reflection of the excitation light EL on the principal surface 11. Hence, interference due to stray light can be avoided by preventing only the reflected light RL, which is obtained from regular reflection of the excitation light EL by the principal surface 11, from being mixed into the light receiving optical system 30. It is difficult to separate scattering light, which has low directivity and is uniformly produced, by setting the optical path, and when scattering light occurs, it is necessary to use an expensive filter. In this embodiment, however, the occurrence of scattering light can be prevented, it is unnecessary to set a filter. This achieves reduction in size and cost of the apparatus.

Particles 100 are collected in the excitation-light irradiation region 104. The particles 100 include biogenic particles 101 such as microorganisms, and non-biogenic dust 102 such as lint of chemical fiber. In FIG. 5, an arrow denoted by symbol F represents fluorescence emitted from the particles 100. Fluorescence F is emitted in all directions from portions of surfaces of the particles 100 irradiated with excitation light EL. Fluorescence F traveling toward the light receiving optical system 30 is collected through the Fresnel lens 32, and is received by the light receiving element 34. By using the Fresnel lens 32 as the light collecting lens for collecting the fluorescence F, the thickness of the light collecting lens can be reduced. This achieves reduction in size and weight of the particle detector 1.

The fluorescence F is emitted in all directions with no directivity from the particles 100 irradiated with the excitation light EL. Part of the fluorescence F directly travels from the particles 100 toward the Fresnel lens 32, and another part of the fluorescence F is emitted from the particles 100 toward the principal surface 11 of the substrate 10. When the principal surface 11 is a mirror surface, the fluorescence F is specularly reflected by the principal surface 11, and the reflected fluorescence F travels toward the Fresnel lens 32. Hence, the intensity of the fluorescence F collected by the Fresnel lens 32 and received by the light receiving element 34 can be increased. This can improve the detection sensitivity of the light receiving element 34 to the fluorescence F.

When the Fresnel lens 32 is disposed at a position at the distance T from the principal surface 11 of the substrate 10, the excitation light EL traveling toward the principal surface 11 of the substrate 10 and the reflected light RL reflected by the principal surface 11 do not enter the Fresnel lens 32. Light that enters the Fresnel lens 32 is limited to only fluorescence F emitted from the particles 100, and neither the excitation light EL nor the reflected light RL is collected by the Fresnel lens 32. The light receiving optical system 30 is disposed at a position such that the excitation light EL and the reflected light RL do not enter the Fresnel lens 32 and the light receiving element 34 does not receive the excitation light EL and the reflected light RL. By doing this, the excitation light EL and the reflected light RL can be reliably separated from the fluorescence F, and the excitation light EL or the reflected light RL can be prevented from becoming noise in detection of the fluorescence F. Hence, the detection sensitivity to the fluorescence F can be improved.

Figure 7:
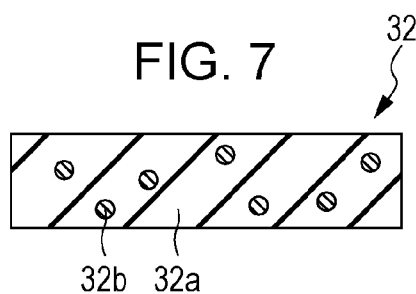
FIG. 7 schematically illustrates a cross section of a Fresnel lens.

FIG. 7 schematically illustrates a cross section of the Fresnel lens 32. The Fresnel lens 32 is formed of a material containing a matrix 32a and absorbent 32b finely dispersed in the matrix 32a. The matrix 32a is formed of an arbitrary material that can be used as the Fresnel lens 32, and for example, may be formed of an acrylic material or a glass material that transmits fluorescence F. The absorbent 32b absorbs a light beam including a wavelength of excitation light EL. The absorbent 32b prevents the light beam including the wavelength of the excitation light EL from passing through the Fresnel lens 32. The Fresnel lens 32 has a filtering function for cutting off the excitation light EL and the reflected light RL.

Figure 8:
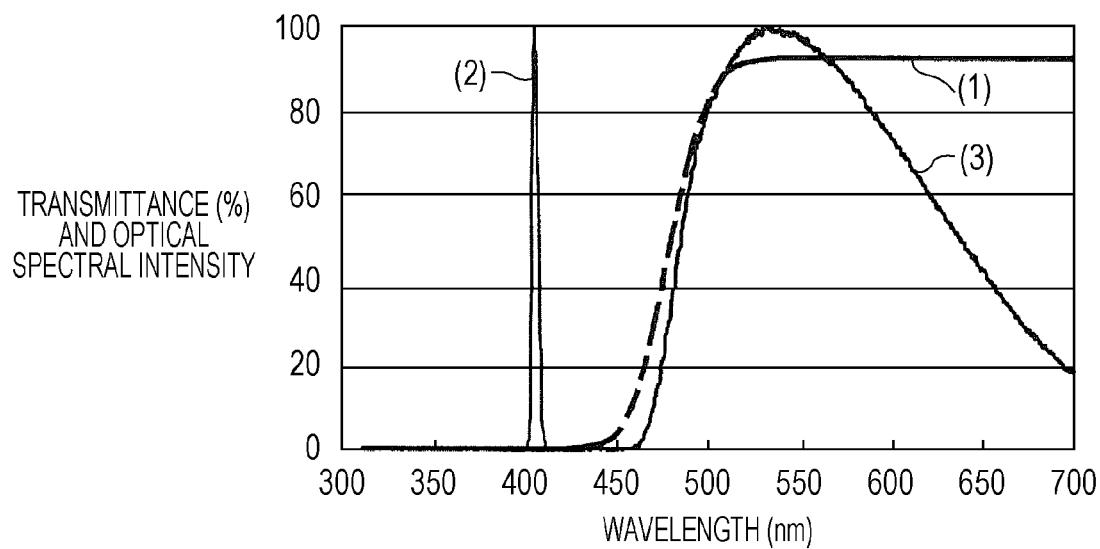
FIG. 8 is a graph showing filter characteristics of absorbent.

FIG. 8 is a graph showing filter characteristics of the absorbent 32b. The horizontal axis in the graph of FIG. 8 indicates the wavelength of light. The unit of the wavelength is nm. The vertical axis in the graph of FIG. 8 indicates the transmittance of the filter and the spectral intensity of light. The unit of transmittance of the filter is %. The spectral intensity of light refers to the relative value of spectral intensity at each wavelength when the wavelength such that the spectral intensity of excitation light EL or fluorescence F becomes the highest is 100. In FIG. 8, curve (1) shows the filter characteristics, curve (2) shows the spectral intensity of excitation light EL from the semiconductor laser element, and curve (3) shows the spectral intensity of fluorescence F emitted from *Penicillium* irradiated with the excitation light EL.

According to the filter characteristics shown by curve (1), the absorbent 32b has the property of cutting off most of light with a wavelength of about 440 nm or less and transmitting most of light with a wavelength of about 500 nm or more. The absorbent 32b has the property as a highpass filter (or a low-cut filter) for cutting off light with a wavelength of a predetermined threshold value or less and transmitting light with a wavelength of the threshold value or more.

As shown by curve (2), excitation light EL from the semiconductor laser has the peak value of optical spectral intensity at a wavelength of about 400 nm, and the spectrum is not measured in the other wavelength ranges. In contrast, as shown by curve (3), the spectrum of fluorescence F from *Penicillium* is measured in a wavelength range more than or equal to about 460 nm, and the fluorescence F has the peak value of optical spectral intensity at a wavelength of about 530 nm.

Since the absorbent 32b having the filter characteristics shown by curve (1) is dispersed in the Fresnel lens 32, when excitation light EL having the optical spectral intensity shown by curve (2) enters the Fresnel lens 32, it is absorbed and cut off by the absorbent 32b. In contrast, when the fluorescence F having the optical spectral intensity shown by curve (3) enters the Fresnel lens 32, it passes through the Fresnel lens 32 while mostly maintaining the optical spectral intensity.

By providing the Fresnel lens 32 with such a filter function, even if the excitation light EL or the reflected light RL erroneously enters the Fresnel lens 32, it can be cut off by the Fresnel lens 32. Thus, since a structure in which fluorescence F selectively passes through the Fresnel lens 32 is provided, noise is prevented from entering the light receiving element 34 for detecting the fluorescence F, and the detection sensitivity to the fluorescence F can be improved. Since the Fresnel lens 32 itself has the filter function, it is unnecessary to provide a filter separate from the Fresnel lens 32, and the structure can be simplified and is made inexpensive.

Figure 9:
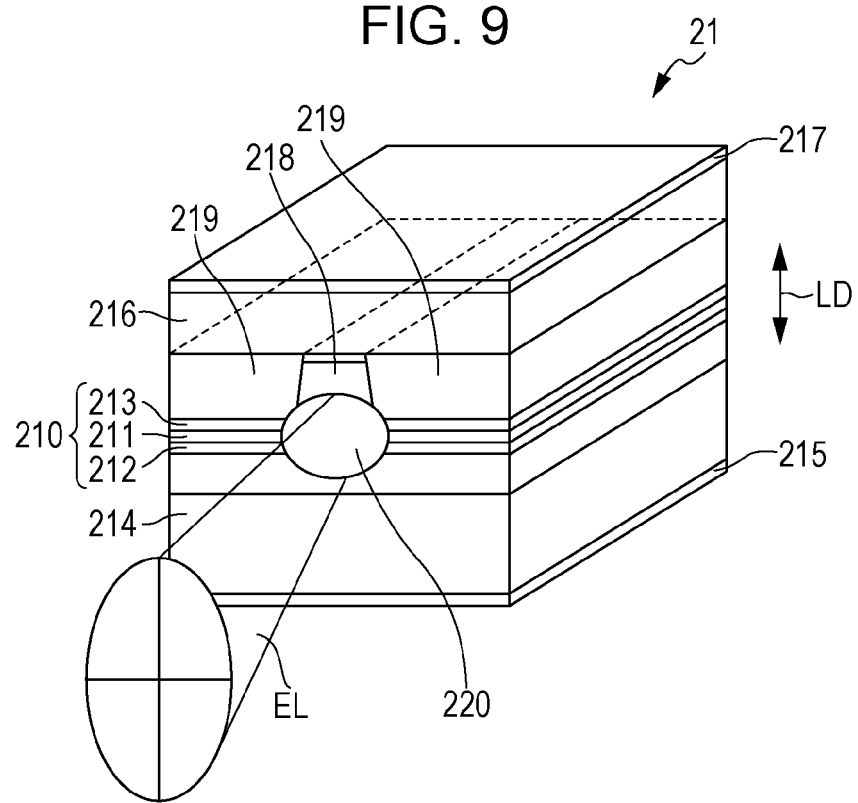
FIG. 9 schematically illustrates radiation characteristics of light emitted from a semiconductor laser element.

FIG. 9 schematically illustrates radiation characteristics of light emitted from the semiconductor laser element. The semiconductor laser element serving as the light emitting element 21 of the embodiment is of an edge-emitting type having a multilayer structure including a light emitting layer. The semiconductor laser element is formed by stacking a substrate 214 formed of n-type GaAs, a lower cladding layer 212 formed of n-type AlGaInP, an active layer 211 formed by a multiquantum well, an upper cladding layer 213 formed of p-type AlGaInP, and a contact layer 216 formed of p-type GaAs. The lower cladding layer 212, the active layer 211, and the upper cladding layer 213 constitute a multilayer structure 210. A stacking direction of the semiconductor layers that constitute the multilayer structure 210 is shown by a two-headed arrow denoted by symbol LD in FIG. 9.

The semiconductor laser element further includes an n-type electrode 215 provided on the substrate 214, a p-type electrode 217 provided on the contact layer 216, a ridge stripe 218, and current block layers 219 formed of n-type AlInP. The ridge stripe 218 and the current block layers 219 are disposed between the multilayer structure 210 and the contact layer 216.

A light emitting part 220 from which excitation light EL is emitted includes the active layer 211. The light emitting part 220 is long sideways on a light emitting surface of the semiconductor laser element. For example, the light emitting part 220 can be formed such that a ratio obtained by dividing the dimension of the light emitting part 220 in the width direction orthogonal to the stacking direction LD by the thickness of the active layer 211 is 50 or more. The semiconductor laser element including such a striped light emitting part 220 constitutes a so-called broad area (BA) semiconductor laser.

In the BA semiconductor laser element, the light emitting part 220 is long sideways, and has a narrow space in a vertical direction. Hence, light emitted from the light emitting part 220 spreads while bending around owing to a diffraction effect. For this reason, emitted excitation light EL spreads such that a spread in the stacking direction LD of the multilayer structure 210 of the semiconductor layers is more than a spread in the width direction orthogonal to the stacking direction LD. Owing to the above-described light diffraction effect, the radiation characteristic of the excitation light EL emitted from the BA semiconductor laser element is band-shaped such that the spread angle of the excitation light EL is large in the stacking direction LD of the semiconductor layers but is small in the width direction orthogonal to the stacking direction.

That is, the radiation characteristic of excitation light EL emitted from the edge-emitting semiconductor laser element is shaped like a band that extends long in the stacking direction LD of the multilayer structure 210 of the semiconductor layers. The excitation light EL emitted from the semiconductor laser element has the property of spreading comparatively wide in the stacking direction LD of the semiconductor layers and spreading comparatively narrow in the width direction. For this reason, the ratio obtained by dividing the dimension of the excitation light EL in the stacking direction LD of the semiconductor layers by the dimension of the excitation light EL in the width direction on a plane parallel to the light emitting surface of the semiconductor layer element increases as the light beam travels away from the semiconductor laser element. Accordingly, the semiconductor laser element is disposed such the band-shaped excitation light EL forms an excitation-light irradiation region 104 of the optimal shape on the principal surface 11 of the substrate 10.

Figure 10:
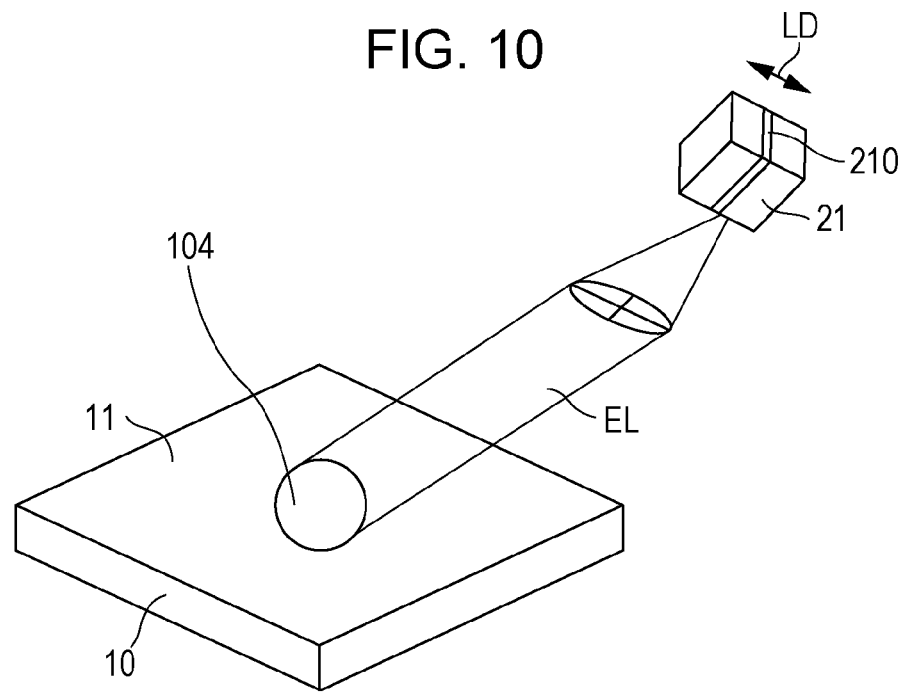
FIG. 10 schematically illustrates an arrangement of the semiconductor laser element based on the radiation characteristics of laser light.

FIG. 10 schematically illustrates an arrangement of the semiconductor laser element based on the radiation characteristics of laser light. As illustrated in FIG. 10, the light emitting element 21 formed by the semiconductor laser element having the multilayer structure 210 of the semiconductor layers, which includes the active layer 211 serving as a light emitting layer, is disposed such that the stacking direction LD of the semiconductor layers extends in the extending direction of the principal surface 11 and the stacking direction LD is parallel to the principal surface 11 of the substrate 10.

By thus arranging the BA semiconductor laser element, the light longitudinal direction in which the excitation light EL emitted from the semiconductor laser element spreads in a band form can be made parallel to the principal surface 11 of the substrate 10. The excitation light EL is applied onto the principal surface 11 of the substrate 10 in a direction at an angle to the principal surface 11, and the excitation light EL spreading in the band form is thereby spread in a lateral direction of the band on the principal surface 11 of the substrate 10. The excitation light EL is applied to the principal surface 11 such that the spread in the longitudinal direction and the spread in the lateral direction are substantially equal, and forms an excitation-light irradiation region 104 of a symmetrical shape.

For example, the semiconductor laser element, which emits excitation light EL schematically spreading in an oval shape in FIGS. 9 and 10, is disposed such that the stacking direction LD of the semiconductor layers is parallel to the principal surface 11 of the substrate 10. Since the excitation light EL is thereby spread in the lateral direction of the oval on the principal surface 11 of the substrate 10, the excitation-light irradiation region 104 formed on the principal surface 11 is shaped like a substantially perfect circle. For this reason, the area of the excitation-light irradiation region 104 can be reduced, and the density of the excitation light EL applied to particles 100 collected on the principal surface 11 can be increased. Therefore, the intensity of fluorescence F emitted from the particles 100 can be increased, and the detection accuracy of the light receiving element 34 to the fluorescence F can be improved. This allows the number of particles 100 to be detected with high sensitivity.

Preferably, the excitation light EL is applied onto an area on the principal surface 11 that extends to some degree so as to form an excitation-light irradiation region 104 having a predetermined area. By forming the excitation-light irradiation region 104 that extended on the principal surface 11, the excitation light EL can be applied to more particles 100 of the particles 100 collected on the principal surface 11 of the substrate 10. Hence, the detection accuracy of the particles can be improved. In contrast, when the excitation light EL is applied to an area outside the principal surface 11 of the substrate 10, it scatters and becomes stray light. This stray light decreases the detection accuracy of fluorescence F. To prevent the occurrence of such stray light, it is necessary to apply all of the excitation light EL onto the substrate 10. In this case, if the excitation-light irradiation region 104 extends wide, the substrate 10 needs to be increased in size. This increases the size of the particle detector 1.

Accordingly, as illustrated in FIG. 10, when the excitation light EL is made circular on the principal surface 11 of the substrate 10 to form a circular excitation-light irradiation region 104, a decrease in detection accuracy of the fluorescence F can be prevented, and an increase in size of the apparatus can be suppressed. Hence, it is possible to provide a particle detector 1 that has high detection accuracy and is suitable for size reduction.

Figure 11:
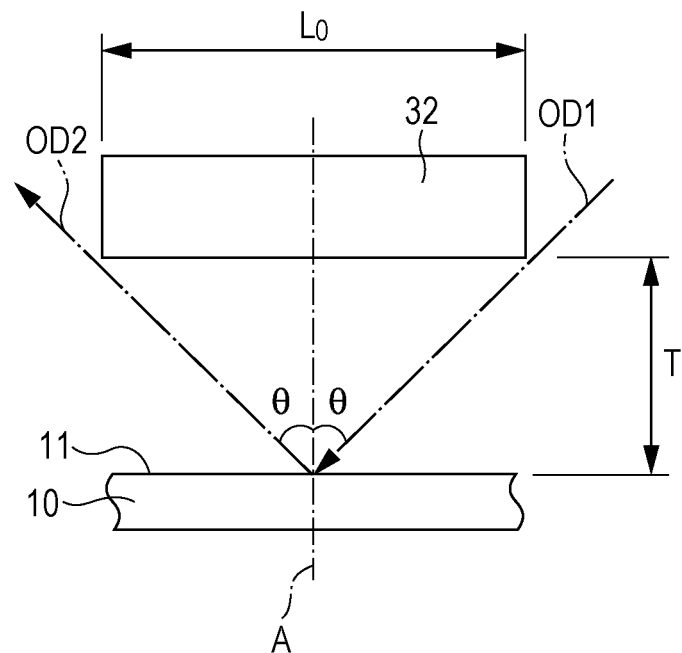
FIG. 11 is a first schematic view illustrating an arrangement of the Fresnel lens relative to the substrate.
Figure 12:
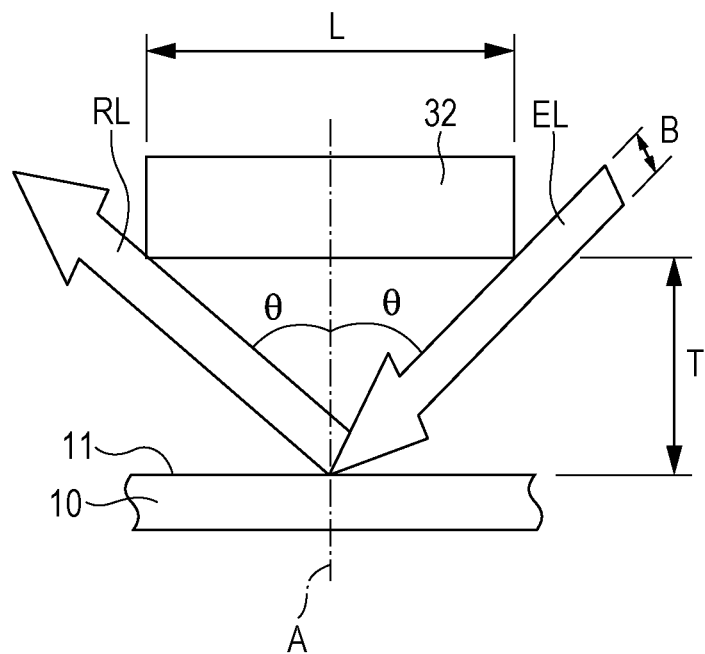
FIG. 12 is a second schematic view illustrating an arrangement of the Fresnel lens relative to the substrate.
Figure 13:
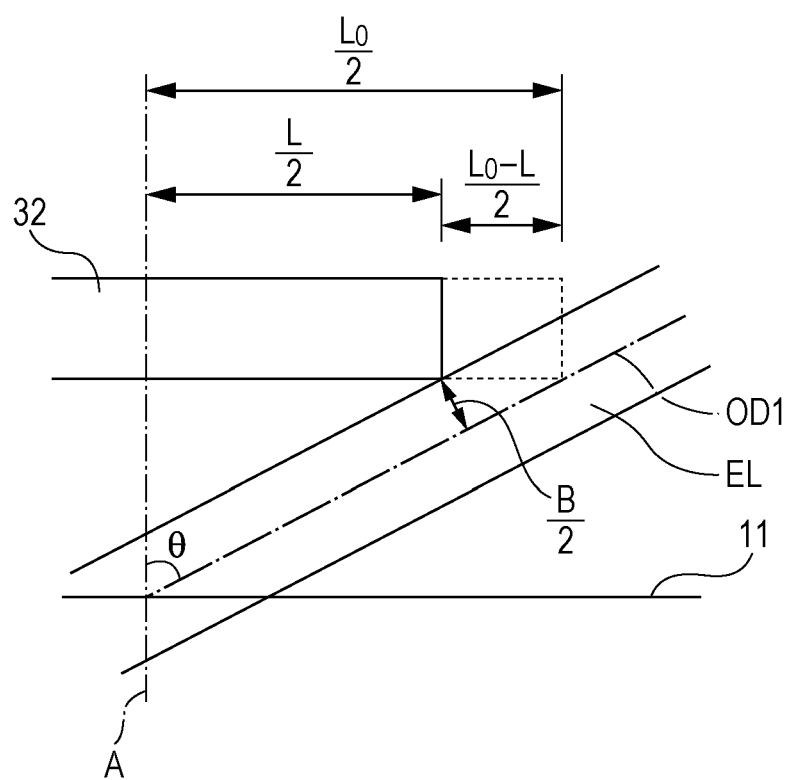
FIG. 13 is a third schematic view illustrating an arrangement of the Fresnel lens relative to the substrate.

FIGS. 11 to 13 schematically illustrate the arrangement of the Fresnel lens 32 relative to the substrate 10. As illustrated in FIG. 11, when it is assumed that excitation light EL and reflected light RL do not have a spread in the ray direction and have a diameter of about 0, the excitation light EL is representatively shown by the ray direction OD1, and the reflected light RL is representatively shown by the ray direction OD2. The excitation light EL enters the principal surface 11 of the substrate 10 at an incident angle θ. Since the principal surface 11 is formed as a mirror surface, the excitation light EL is regularly reflected by the principal surface 11, and the reflected light RL is reflected at a reflection angle θ equal to the incident angle.

When the diameter of the excitation light EL and the reflected light RL is about 0, the Fresnel lens 32 is formed to have a diameter $L_0$. To prevent the excitation light EL whose incident angle is θ and the reflected light RL whose reflection angle is θ from interfering with the Fresnel lens 32 having the diameter $L_0$, the Fresnel lens 32 is disposed at a position at a distance T from the principal surface 11 of the substrate 10. In this case, a relationship $\tan θ = (L_0/2)/T = L_0/2T$ is established.

FIGS. 12 and 13 show conditions where excitation light EL and reflected light RL do not interfere with the Fresnel lens 32 disposed at the distance T from the principal surface 11, similarly to FIG. 11, when they have a diameter B. Since the excitation light EL and the reflected light RL have spreads in the ray directions OD1 and OD2, respectively, the Fresnel lens 32 is formed to have a diameter L that is less than the diameter $L_0$ in FIG. 11.

In this case, referring to FIG. 13, when a relationship $(B/2)/\{(L_0-L)/2\} = \cos θ$ is established and arranged so that $L_0 = B/\cos θ + L$. When this relational expression is substituted in the above-described expression, $\tan θ = (B/\cos θ + L)/2T$. After all, the distance T between the substrate 10 and the Fresnel lens 32 is represented as a function of the angle θ by $T = (B/\cos θ + L)/2 \tan θ$. This distance T refers to the minimum distance by which the Fresnel lens 32 needs to be disposed to be apart from the principal surface 11 of the substrate 10 to prevent interference of the excitation light EL and the reflected light RL with the Fresnel lens 32 when the Fresnel lens 32 has the diameter L, the excitation light EL has the diameter B, and the excitation light EL has the incident angle θ.

That is, in order for the excitation light EL and the reflected light RL not to interfere with the Fresnel lens 32, the Fresnel lens 32 is disposed at a distance more than or equal to the distance T found by the above expression from the principal surface 11 of the substrate 10. In contrast, as the distance of the Fresnel lens 32 from the substrate 10 decreases, the size of the optical system can decrease, and therefore, the size of the particle detector 1 can decrease. In addition, as the distance of the Fresnel lens 32 from the particles 100 collected on the principal surface 11 of the substrate 10 decreases, the receiving efficiency for fluorescence F emitted from the particles 100 increases, and the detection accuracy of the fluorescence F increases. This is because the fluorescence F is emitted in all directions with no directivity from the particles 100, and the fluorescence F can be received in an increasing angle range as the distance of the Fresnel lens 32 to the particles 100 decreases. Therefore, the relative position between the Fresnel lens 32 and the substrate 10 is preferably determined such that the relationship $T = (B/\cos θ + L)/2 \tan θ$ is established between the distance T and the angle θ.

By increasing the incident angle θ of the excitation light EL and decreasing the inclination of the excitation light EL from the principal surface 11, the distance T found by $T = (B/\cos θ + L)/2 \tan θ$ is decreased. That is, as the incident angle θ of the excitation light EL increases, the reflected light RL becomes less likely to enter the Fresnel lens 32 even when the Fresnel lens 32 is located closer to the substrate 10. Hence, the Fresnel lens 32 can be disposed closer to the substrate 10, and this can further reduce the size of the particle detector 1. For example, the incident angle θ is preferably set to be within a range not less than 60°.

However, if the incident angle θ is too large, the ray direction OD1 of the excitation light EL approaches the direction parallel to the principal surface 11. For this reason, the particles 100 collected at a position close to the excitation optical system 20 are irradiated with the excitation light EL, whereas the particles 100 collected at a position apart from the excitation optical system 20 are hidden by the particles 100 close to the excitation optical system 20, and are not irradiated with the excitation light EL. In this case, since all of the particles 100 collected on the substrate 10 do not emit fluorescence F, fluorescence F having an intensity corresponding to the collected number of particles 100 on the substrate 10 cannot be detected, and this reduces the detection accuracy of the number of particles. Therefore, for example, the incident angle θ is preferably set to be within a range not more than 70°.

[Operation of Particle Detector]

Figure 14:
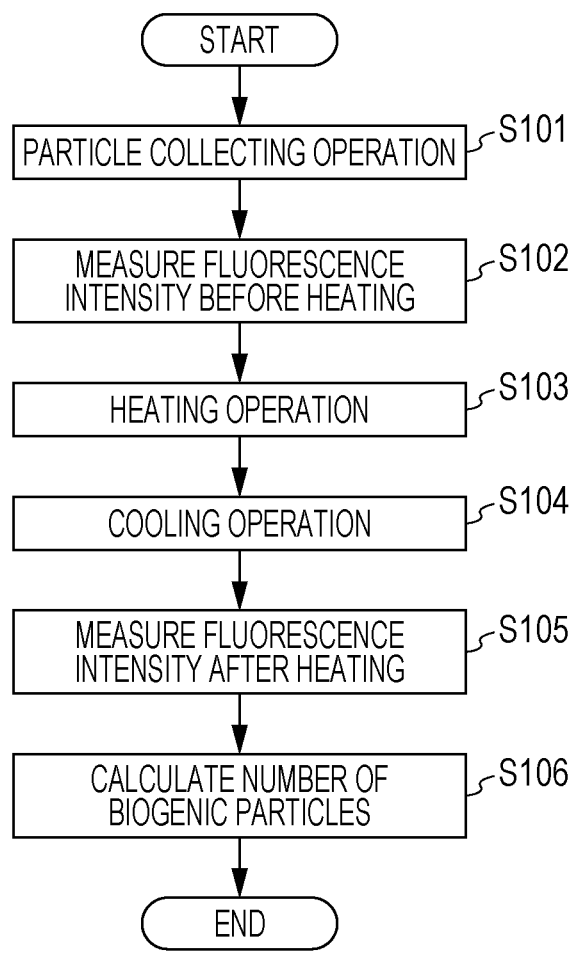
FIG. 14 is a flowchart showing a flow of operations of the particle detector.

A description will be given of operations for detecting the number of biogenic particles 101 with the particle detector 1 having the above-described configuration. FIG. 14 is a flowchart showing a flow of operations of the particle detector 1.

Referring to FIG. 14, first, particles 100 are collected on the principal surface 11 of the substrate 10 (S101). At this time, air is introduced into the cabinet of the particle detector 1 through the introducing portion 3 by driving the fan 92 in a forward direction to form an airflow traveling toward the principal surface 11 of the substrate 10. In addition, the electrostatic probe 62 is positioned opposed to the principal surface 11 of the substrate 10, and a potential difference is produced between the electrostatic probe 62 and the substrate 10 by the collection power-supply circuit 61. Particles 100 suspended in the air are thereby charged, and the charged particles 100 are collected onto the principal surface 11 of the substrate 10 by electrostatic force.

Next, the excitation optical system 20 applies excitation light EL to the particles 100 collected on the substrate 10, and the light receiving optical system 30 receives fluorescence F emitted from the particles 100 upon irradiation with the excitation light EL. The light emitting element 21 formed by the semiconductor laser element applies excitation light EL to the particles 100, and the light receiving element 34 receives fluorescence F emitted from the particles 100 at this time via the Fresnel lens 32. The fluorescence intensity before heating of the particles 100 collected on the substrate 10 is thereby measured (S102).

Next, the particles 100 collected on the substrate 10 are heated by energizing the heater 91 (S103). Next, energization of the heater 91 is stopped, and the substrate 10 is cooled (S104). At this time, air is introduced into the cabinet of the particle detector 1 through the fan 92 to promote cooling of the substrate 10 by driving the fan 92 in a reverse direction.

Next, the excitation optical system 20 applies excitation light EL onto the particles 100 collected on the substrate 10, and the light receiving optical system 30 receives fluorescence F emitted from the particles 100 upon irradiation with the excitation light EL. The fluorescence intensity after heating of the particles 100 collected on the substrate 10 is thereby measured (S105). By comparing the intensity of the fluorescence F before heating and the intensity of the fluorescence F after heating, the number of biogenic particles 101 included in the particles 100 collected on the substrate 10 is calculated (S106).

Figure 15:
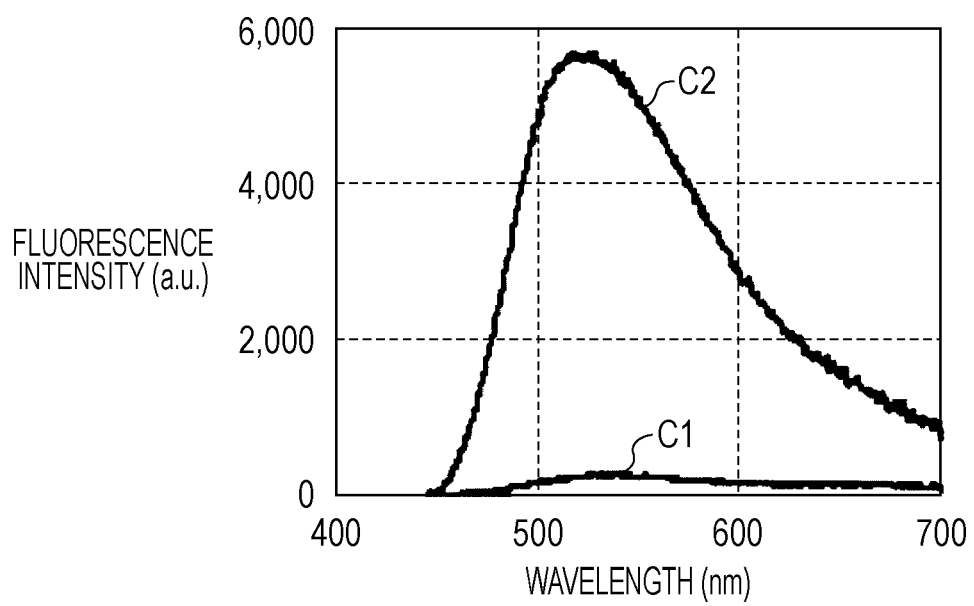
FIG. 15 shows the time change of a fluorescence spectrum of *Penicillium* before and after heat treatment.

FIG. 15 shows a time change of a fluorescence spectrum of *Penicillium* before and after heat treatment. FIG. 15 shows measurement results of the fluorescence spectrum before heat treatment (curve C1) and after heat treatment (curve C2) when *Penicillium* is heated as examples of biogenic particles 101 at 200° C. for five minutes. These results show that the intensity of fluorescence from the *Penicillium* is greatly increased by conducting heat treatment.

Figure 16:
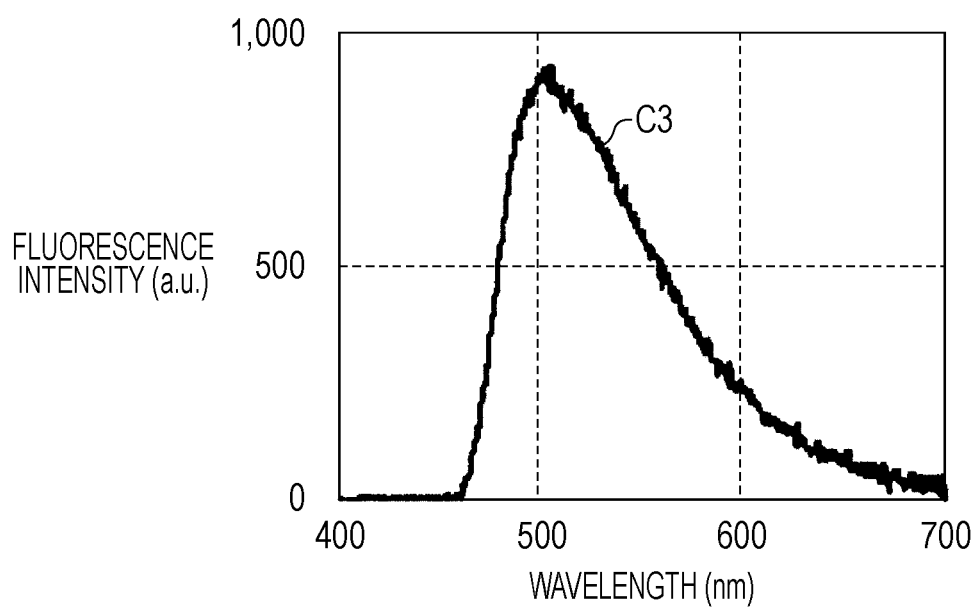
FIG. 16 shows a fluorescence spectrum of fluorescence-emitting dust before heat treatment.
Figure 17:
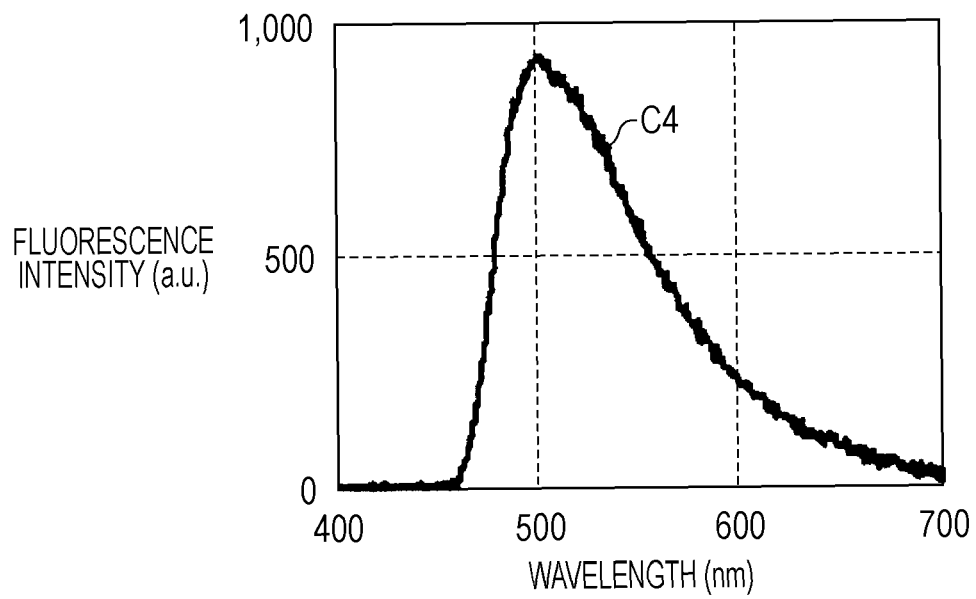
FIG. 17 shows a fluorescence spectrum of the fluorescence-emitting dust after heat treatment.

FIG. 16 shows a fluorescence spectrum of fluorescence-emitting dust before heat treatment. FIG. 17 shows a fluorescence spectrum of the fluorescence-emitting dust after heat treatment. FIG. 16 and FIG. 17 show measurement results of the fluorescent spectrum before heat treatment (curve C3) and after heat treatment (curve C4), respectively, when the fluorescence-emitting dust is heated at 200° C. for five minutes. It is verified that the fluorescence spectrum shown by curve C3 and the fluorescence spectrum shown by curve C4 are nearly aligned with each other. That is, it is known that the intensity of fluorescence from the dust does not change before and after heat treatment.

When the biogenic particles 101 suspended in the air are irradiated with ultraviolet light or blue light, they emit fluorescence F. However, dust 102 that similarly emits fluorescence, such as lint of chemical fiber, is suspended in the air. Hence, when only the fluorescence F is detected, it is not determined whether the fluorescence F is emitted from the biogenic particles 101 or the dust 102.

On the other hand, when the biogenic particles 101 and the dust 102 are subjected to heat treatment and changes in the fluorescence intensity (fluorescent amount) before and after heating are measured, the intensity of fluorescence emitted from the dust 102 is not changed by heat treatment, whereas the intensity of fluorescence emitted from the biogenic particles 101 is increased by heat treatment. In the particle detector 1 of the embodiment, the fluorescence intensity of the particles 100, in which the biogenic particles 101 and the dust 102 are mixed, is measured before and after heating, and a difference between the measured fluorescence intensities is found to specify the number of biogenic particles 101.

The intensity of fluorescence F emitted from the biogenic particles 101 is increased by heat treatment. For this reason, in Step (S105), a fluorescence intensity higher than the fluorescence intensity measured before heating in Step (S102) is measured. An increase amount in fluorescence intensity is calculated from the difference between the fluorescence intensity before heating and the fluorescence intensity after heating. On the basis of a prepared relationship between the increase amount in fluorescence intensity and the concentration of biogenic particles, the concentration of biogenic particles 101 corresponding to the calculated increase amount can be specified. The correspondence relationship between the increase amount and the concentration of biogenic particles is experimentally determined beforehand.

[Configuration of Particle Removing Apparatus]

Figure 18:
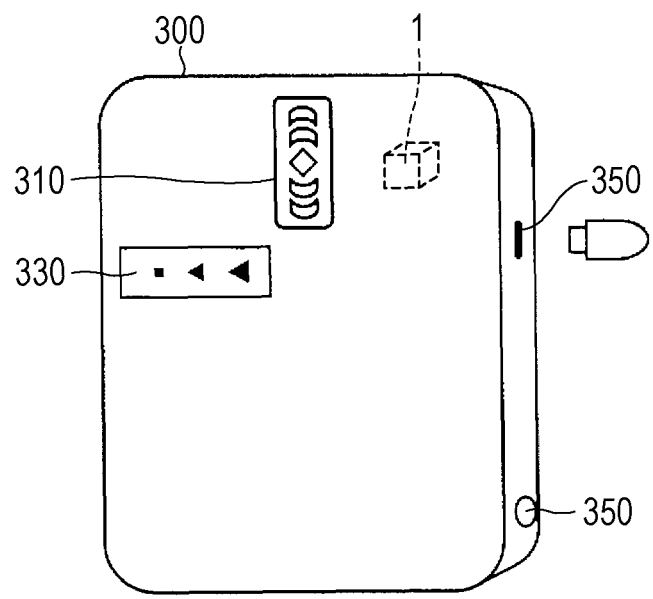
FIG. 18 illustrates an exemplary appearance of an air purifier including the particle detector.

The particle detector 1 of the embodiment may be used alone as an apparatus for detecting biogenic particles 101, or may be incorporated in home electric appliances such as an air purifier, an air conditioner, a humidifier, a dehumidifier, a vacuum cleaner, a refrigerator, and a television. FIG. 18 illustrates an exemplary appearance of an air purifier 300 including the particle detector 1. The air purifier 300 is an example of a particle removing apparatus that efficiently removes biogenic particles 101 detected by the particle detector 1.

The air purifier 300 includes a switch 310 that receives operation instructions, and a display panel 330 that displays detection results and the like. The air purifier 300 also includes other unillustrated elements such as a suction opening through which air is introduced and an exhaust opening through which air is exhausted. The air purifier 300 further includes a communication unit 350 in which a recording medium is loaded. The communication unit 350 may provide connection to a communication line for communicating with other apparatuses through the Internet. Alternatively, the communication unit 350 may communicate with other apparatuses, for example, through infrared communication or through the Internet. The particle detector 1 is disposed in a housing of the air purifier 300. The air purifier 300 can efficiently purify ambient air by virtue of the particle detector 1 that can accurately detect biogenic particles 101 and can achieve size reduction.

Figure 19:
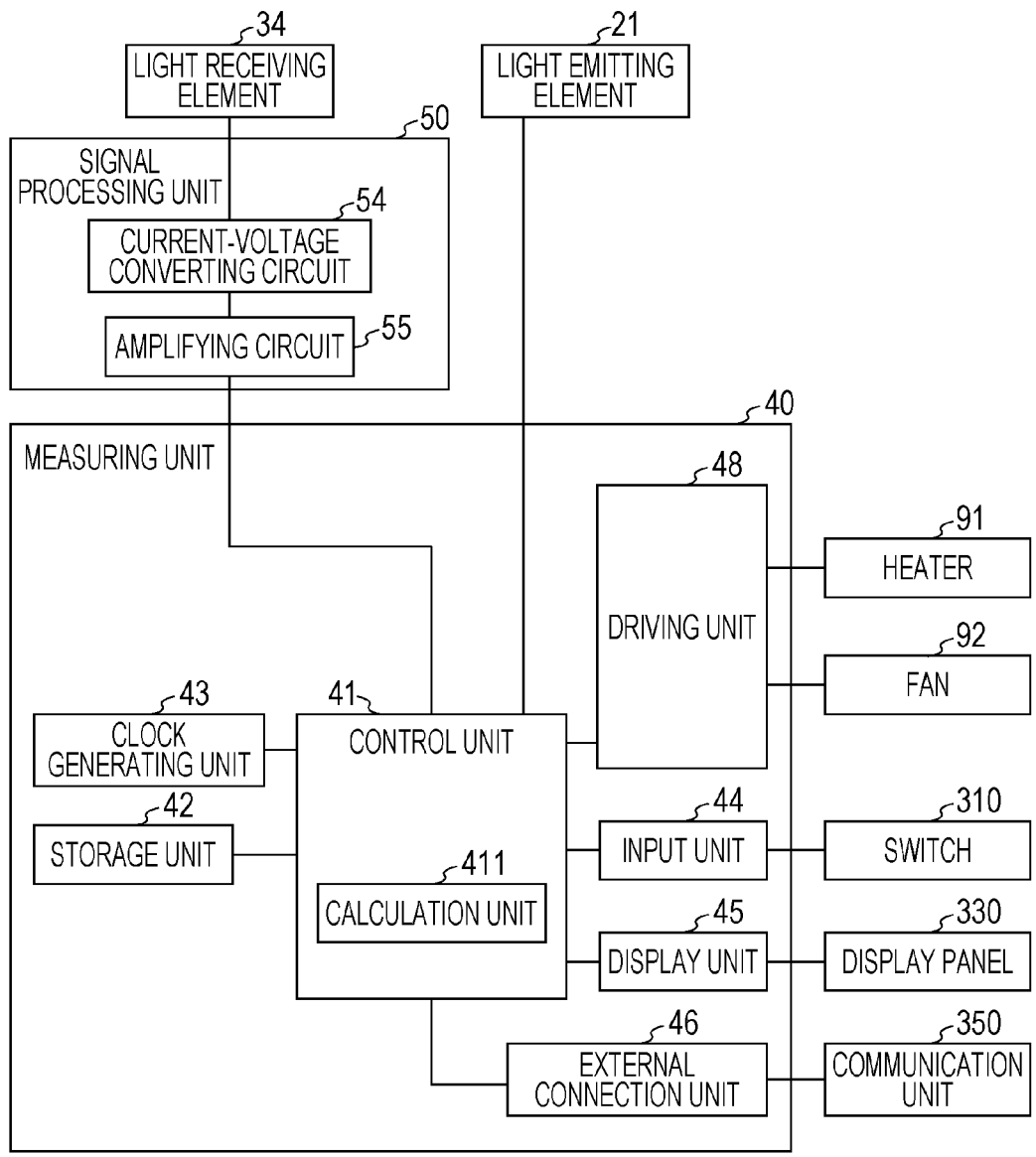
FIG. 19 is a block diagram showing an exemplary functional configuration of the air purifier.

FIG. 19 is a block diagram of an exemplary functional configuration of the air purifier 300. FIG. 19 illustrates an example in which the functions of a signal processing unit 50 are implemented by hardware configuration mainly of electric circuitry. However, at least part of these functions may be implemented by software configuration realized by an unillustrated CPU (Central Processing Unit) included in the signal processing unit 50 to execute a predetermined program. Further, FIG. 19 illustrates an example in which a measuring unit 40 is implemented by software configuration. However, at least part of the functions may be realized by hardware configuration such as electric circuitry.

Referring to FIG. 19, the signal processing unit 50 includes a current-voltage converting circuit 54 connected to the light receiving element 34, and an integrating amplifying circuit 55 connected to the current-voltage converting circuit 54.

The measuring unit 40 includes a control unit 41, a storage unit 42, and a clock generating unit 43. The measuring unit 40 further includes an input unit 44 that receives information input by receiving an input signal from a switch 310 upon operation of the switch 310, a display unit 45 that executes processing for displaying, for example, measurement results on the display panel 330, an external connection unit 46 that executes processing necessary for exchanging data and the like with an external apparatus connected to the communication unit 350, and a driving unit 48 that drives the fan 92 and the heater 91.

When particles 100 collected on the principal surface 11 of the substrate 10 are irradiated with excitation light EL from the light emitting element 21, fluorescence F from the particles 100 in the excitation-light irradiation region 104 is collected at the light receiving element 34. The light receiving element 34 outputs a current signal in accordance with the amount of received light to the signal processing unit 50. The current signal is input to the current-voltage converting circuit 54.

The current-voltage converting circuit 54 detects a peak current value H, which represents the fluorescence intensity, from the current signal input from the light receiving element 34, and converts the peak current value H into a voltage value Eh. The voltage value Eh is amplified by a preset gain by the amplifying circuit 55, and is output to the measuring unit 40. The control unit 41 of the measuring unit 40 receives the input of the voltage value Eh from the signal processing unit 50, and stores the input in the storage unit 42 in order.

The clock generating unit 43 generates and outputs clock signals to the control unit 41. With the timing based on the clock signals, the control unit 41 outputs control signals for rotating the fan 92 to the driving unit 48, and controls introduction of air by the fan 92. Further, the control unit 41 is electrically connected to the light emitting element 21 and the light receiving element 34, and controls ON/OFF of these elements.

The control unit 41 includes a calculation unit 411. The calculation unit 411 performs operation for calculating the number of biogenic particles in the introduced air by using the voltage value Eh stored in the storage unit 42.

The concentration of the biogenic particles 101 in the collected particles 100, which is calculated by the calculation unit 411, is output from the control unit 41 to the display unit 45. The display unit 45 performs processing for displaying the input concentration of microorganisms on the display panel 330. For example, the display panel 330 has lamps corresponding to concentrations, and the display unit 45 specifies a lamp corresponding to the calculated concentration as a lamp to be lighted, and lights the lamp. As another example, a lamp may be lighted in different colors according to the calculated concentration. The display on the display panel 330 is not limited to lamp display. Numerical values, concentrations, or messages prepared beforehand corresponding to the concentrations may be displayed. The measurement results may be written on a recording medium loaded in the communication unit 350 or may be transmitted to an external apparatus via the communication unit 350 by the external connection unit 46.

The input unit 44 may receive selection of a display method on the display panel 330 according to an operation signal from the switch 310. Alternatively, the input unit 44 may receive selection of display of the measurement results on the display panel 330 or output of the measurement results to the external apparatus. A signal indicating the contents of selection is output to the control unit 41, and the control unit 41 outputs a necessary control signal to the display unit 45 and/or the external connection unit 46.

The particle detector 1 utilizes the difference in characteristics between fluorescence F from the biogenic particles 101 and fluorescence F from the dust 102 for emitting the fluorescence F due to heat treatment, and detects biogenic particles 101 on the basis of an increase amount after predetermined heat treatment. For this reason, even when dust 102 for emitting fluorescence F is contained in the introduced air, the particle detector 1 accurately detects biogenic particles 101 separate from the dust 102 for emitting fluorescence on a real-time basis.

The air purifier 300 utilizes the concentration of biogenic particles 101 detected by the particle detector 1, and can efficiently remove the biogenic particles 101 by changing the operating state according to the output from the particle detector 1. That is, when the output of the particle detector 1 is large and the concentration of biogenic particles 101 is high, a particle removing ability of the air purifier 300 can be enhanced, for example, by rotating the fan 92 at high speed to increase the ventilation amount. When the output of the particle detector 1 is small and the concentration of biogenic particles 101 is low, the particle removing ability can be reduced. Hence, the rotation number of the fan 92 is decreased to reduce the ventilation amount, and power-saving operation can be achieved.

Although the embodiment of the present invention has been described above, it should be considered that the disclosed embodiment is not restrictive, but is illustrative in all respects. The scope of the present invention is defined by the claims, not by the above description. Further, the scope of the present invention is intended to include all modifications within the meaning and range equivalent to the scope of the claims.

INDUSTRIAL APPLICABILITY

The present invention is used as an apparatus that mainly detects biogenic particles such as pollen, microorganisms, and mold.

REFERENCE SIGNS LIST 1 particle detector
10 substrate
11 principal surface
20 excitation optical system
21 light emitting element
24 light collecting lens
30 light receiving optical system
32 Fresnel lens
32a matrix
32b absorbent
34 light receiving element
100 particle
101 biogenic particle
102 dust
104 excitation-light irradiation region
210 multilayer structure
211 active layer
220 light emitting unit
300 air purifier
A optical axis
B diameter of light
EL excitation light
F fluorescence
L, $L_0$ diameter of lens
LD stacking direction
OD1, OD2 ray direction
RL reflected light
T distance
$\theta$ incident angle.

The invention claimed is:

1. A particle detector that detects biogenic particles, comprising:

a collecting member having a principal surface and configured to collect the biogenic particles on the principal surface;

a light irradiation unit configured to irradiate the particles collected on the principal surface with excitation light emitted from the light irradiation unit in a direction which defines an acute angle relative to the principal surface; and a light receiving unit configured to receive fluorescence emitted from the particles when the particles are irradiated with the excitation light from the light irradiation unit, wherein an optical axis of the light receiving unit and a ray direction of the excitation light intersect with each other, wherein the principal surface is a mirror surface, wherein the light irradiation unit includes an edge-emitting semiconductor laser element, and wherein the semiconductor laser element has a multilayer structure including a light emitting layer, and is disposed such that a stacking direction of the multilayer structure is parallel to the principal surface.

* * * * *